(12) United States Patent
Vadake Kulangara et al.

(10) Patent No.: US 9,938,360 B2
(45) Date of Patent: Apr. 10, 2018

(54) CATALYST COMPRISING A METALLOCENE COMPLEX AND A CO-CATALYST

(71) Applicants: SAUDI BASIC INDUSTRIES CORPORATION, Riyadh (SA); SABIC GLOBAL TECHNOLOGIES B.V., Bergen op Zoom (NL)

(72) Inventors: Shaneesh Vadake Kulangara, Geleen (NL); Nicolaas Hendrika Friederichs, Geleen (NL)

(73) Assignees: SAUDI BASIC INDUSTRIES CORPORATION, Riyadh (SA); SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/121,092

(22) PCT Filed: Mar. 5, 2015

(86) PCT No.: PCT/EP2015/054642
§ 371 (c)(1),
(2) Date: Aug. 24, 2016

(87) PCT Pub. No.: WO2015/132346
PCT Pub. Date: Sep. 11, 2015

(65) Prior Publication Data
US 2017/0240662 A1    Aug. 24, 2017

(30) Foreign Application Priority Data

Mar. 6, 2014 (EP) .................... 14158144
Mar. 6, 2014 (EP) .................... 14158145

(51) Int. Cl.
C08F 4/6592 (2006.01)
C08F 210/16 (2006.01)
C07F 17/00 (2006.01)
C08F 10/02 (2006.01)

(52) U.S. Cl.
CPC ............. *C08F 10/02* (2013.01); *C07F 17/00* (2013.01); *C08F 4/65927* (2013.01); *C08F 210/16* (2013.01)

(58) Field of Classification Search
CPC .......................... C08F 4/65927; C08F 210/16
See application file for complete search history.

(56) References Cited

U.S. PATENT DOCUMENTS 5,132,262 A    7/1992   Rieger et al.
6,096,912 A    8/2000   Karl et al.
6,342,622 B1 * 1/2002   Arts ................. C07F 7/0818
                                                502/103

(Continued)

FOREIGN PATENT DOCUMENTS

JP       07048408        2/1995
WO   WO 2013/091837  *  6/2013

OTHER PUBLICATIONS

Ellis, William W. et al, "Synthesis, Structure, and Properties of Chiral Titanium and Zirconium Complexes Bearing Biaryl Strapped Substituted Cyclopentadienyl Ligands", Organometallics 12, 4391-4401 (1993).
Huttenloch, Monica E., et al., "ansa-Metallocene derivatives XXXIX Biphenyl-bridged metallocene complexes of titanium, zirconium, and vanadium: syntheses, crystal structions and enantioseparation", J. of Organometallic Chemistry 541, pp. 219-232 (1997).

(Continued)

*Primary Examiner* — Caixia Lu
(74) *Attorney, Agent, or Firm* — Cantor Colburn LLP

(57) ABSTRACT

A process for the preparation of ethylene α-olefin copolymers by copolymerizing ethylene with α-olefins in the presence of a catalyst formed by contacting a metallocene complex with a cocatalyst, wherein the metallocene complex is a metallocene complex according to formula I or a metallocene complex according to formula II,

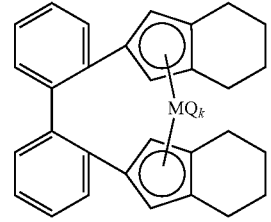

formula I

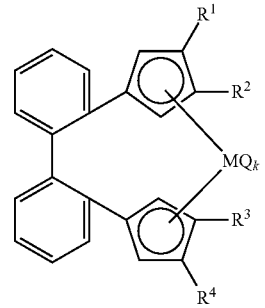

formula II wherein M is chosen from the group of Ti, Zr and Hf; Q is halogen (F, Cl, Br, I) or an alkyl group comprising 1 to 20 carbon atoms; k is the number of Q groups, is an integer and equals the valence of M minus 2; and wherein $R^1$, $R^2$, $R^3$ and $R^4$ are identical or different and can be chosen from alkyl groups with 1-20 carbon atoms.

20 Claims, 4 Drawing Sheets

(56) References Cited

U.S. PATENT DOCUMENTS 6,541,548 B2 4/2003 Weidner
2014/0378694 A1* 12/2014 Al-Humydi ............. C07C 1/321
556/53

OTHER PUBLICATIONS

International Search Report and Written Opinion for PCT/EP2015/054642, dated May 11, 2015, 11 pages.
Peacock, Andrew J., "Production Processes", Handbook of Polyethylene, Marcel Dekker AG (Ed), pp. 43-66 (2000).
Zimm, Bruno and Stockmayer, Walter H., "The Dimensions of Chain Molecules Containing Branches and Rings", The Journal of Chemical Physics, vol. 17, No. 12, pp. 1301-1314 (1949).

* cited by examiner

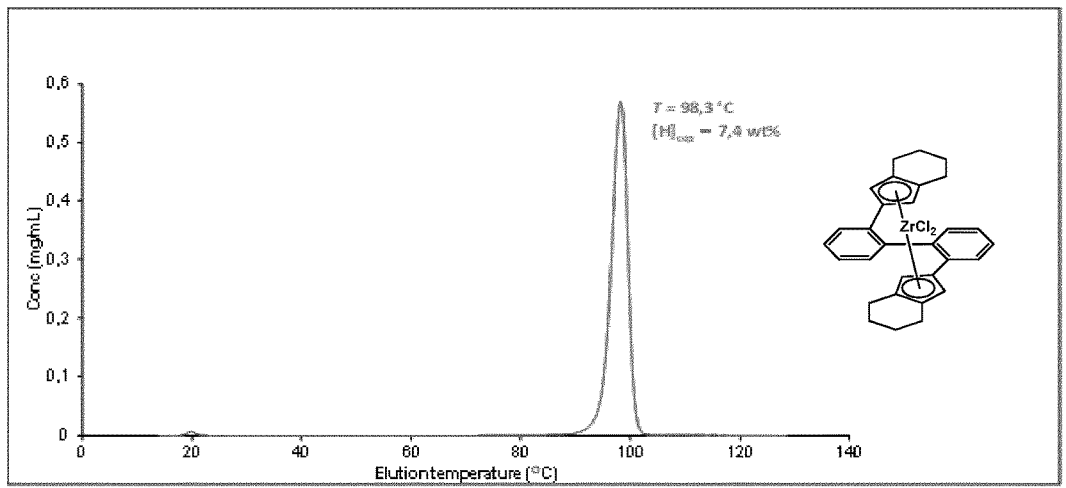
Figure 3: CEF diagram of product prepared with catalyst I
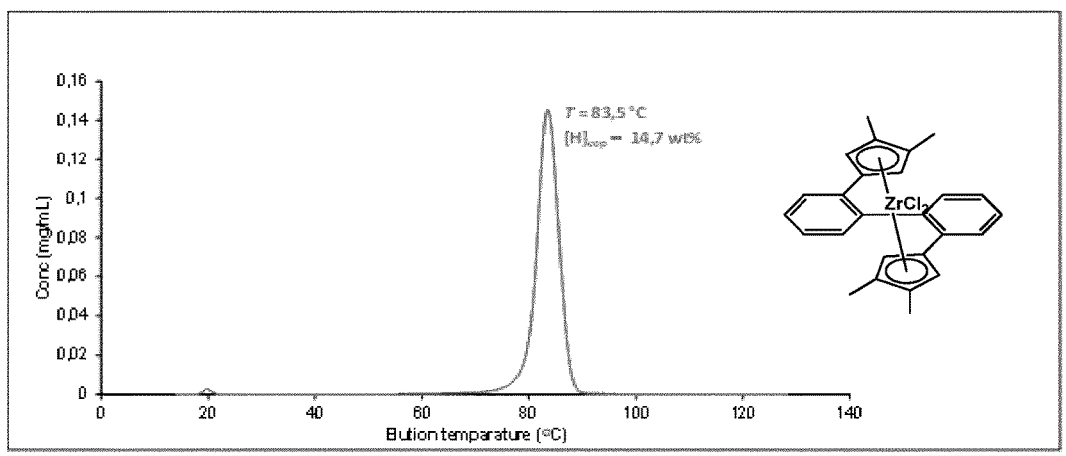
Figure 4: CEF diagram of product prepared with catalyst II

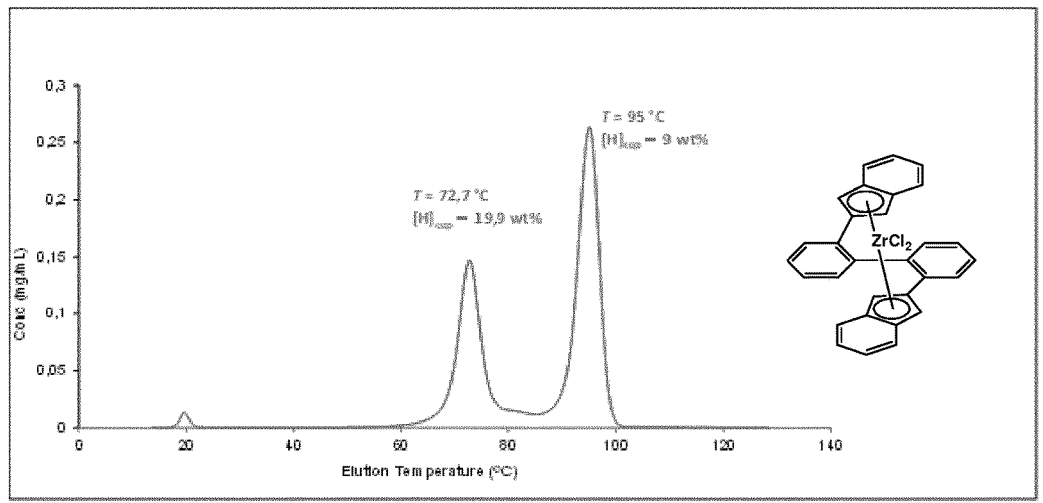
Figure 5: CEF diagram of product prepared with catalyst III
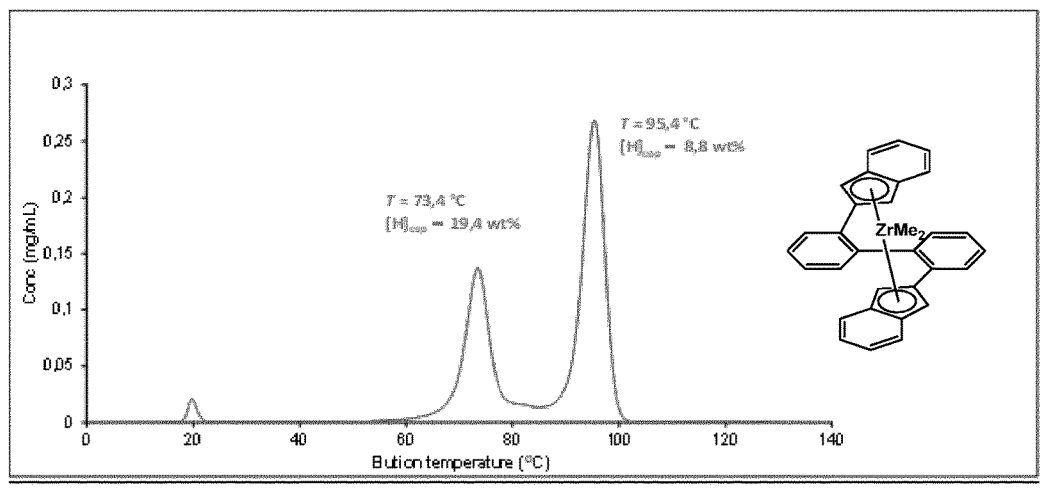
Figure 6: CEF diagram of product prepared with catalyst VI

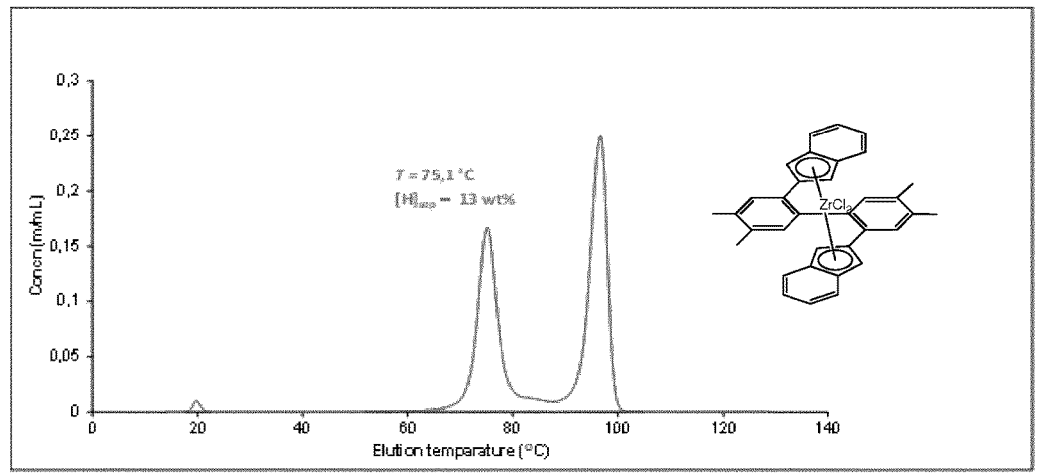
Figure 7: CEF diagram of product prepared with catalyst VIII
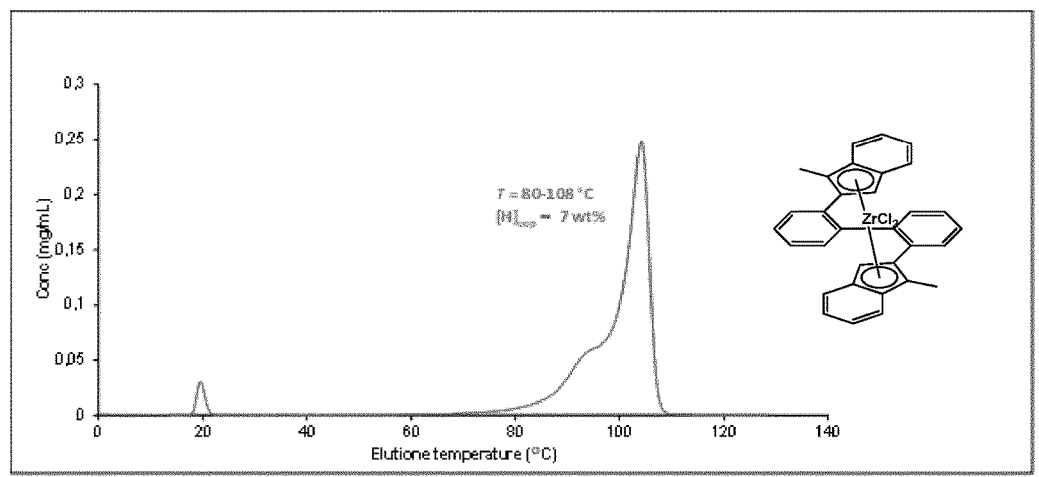
Figure 8: CEF diagram of product prepared with catalyst IX

CATALYST COMPRISING A METALLOCENE COMPLEX AND A CO-CATALYST

This application is a national stage application of PCT/EP2015/054642 filed Mar. 5, 2015, which claims priority to European Patent Applications EP14158145.4 filed Mar. 6, 2014 and EP14158144.7 filed Mar. 6, 2014, all of which are hereby incorporated by reference in their entirety.

The invention relates to a catalyst comprising a metallocene complex, a co-catalyst and optionally an inorganic support material, a process for the preparation of the catalyst, a process for the preparation of ethylene α-olefin copolymers by polymerizing ethylene with one or more α-olefins in the presence of the catalyst and the use of the olefin copolymers.

The catalyst that is used in a process for the preparation of olefin polymers comprises specific bridged metallocene complex. Bridged metallocene complexes are known according to the state of the art and are for instance described in U.S. Pat. Nos. 6,342,622, 6,541,548, 5,132,262 and 6,096,912.

U.S. Pat. No. 6,342,622 describes bridged indenyl metallocene complexes comprising at least one indenyl group and a bridge comprising at least one sp2-hybridized carbon atom that is bonded to the indenyl group at the 2-position.

U.S. Pat. No. 6,541,548 describes bridged bis(tetrahydroindenyl) metallocene complexes wherein a divalent group bridges the two tetrahydroindenyl groups.

U.S. Pat. No. 5,132,262 describes bridged metallocene complexes wherein the bridge comprises silicon or germanium. The metallocene complexes are used for the preparation of propylene homo- and copolymers.

U.S. Pat. No. 6,096,912 describes bridged metallocene complexes wherein the bridge comprises carbon, sulfur, phosphorus, silicon or germanium. The metallocene complexes are used for the preparation of propylene homo- and copolymers.

A disadvantage of known catalysts comprising bridged metallocene complexes is that these catalysts produce low molecular weight copolymers when the catalysts are used for a copolymerization of ethylene with an α-olefin. Also some of the catalysts tend to make inhomogeneous products showing a broad composition distribution and/or a broad molecular weight distribution. There is a need for catalysts that can produce high molecular weight copolymers of ethylene and α-olefins, having a narrow molecular weight distribution and narrow compositional distribution.

The invention relates to a process for the preparation of ethylene α-olefin copolymers by copolymerizing ethylene with α-olefins in the presence of a catalyst formed by contacting a metallocene complex with a cocatalyst, wherein the metallocene complex is chosen from the group consisting of a metallocene complex according to formula I or a metallocene complex according to formula II,

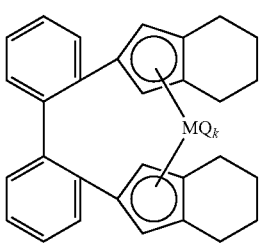

formula I

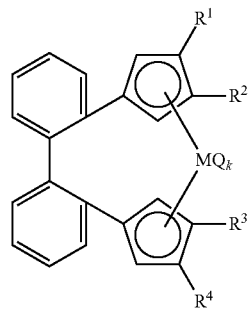

formula II wherein M is chosen from the group of Ti, Zr and Hf; Q is halogen (F, Cl, Br, I) or an alkyl group comprising 1 to 20 carbon atoms; k is the number of Q groups, is an integer and equals the valence of M minus 2; and wherein $R^1$, $R^2$, $R^3$ and $R^4$ are identical or different and can be chosen from alkyl groups with 1-20 carbon atoms, more preferably $R^1$, $R^2$, $R^3$ and $R^4$ are identical or different and are chosen from methyl or ethyl groups, most preferably $R^1$, $R^2$, $R^3$ and $R^4$ are methyl groups.

It has been surprisingly discovered that by using a process according to the invention for the preparation of olefin copolymers, olefin copolymers are obtained with a high weight average molecular weight (Mw), a high number average molecular weight (Mn), narrow polydispersity (molecular weight distribution (Mw/Mn)) and a narrow chemical compositional distribution (CCD).

A further advantage is that the catalysts applied in the process according to the invention can prepare copolymers of ethylene with α-olefins having 3 or more carbon atoms wherein the copolymers have a relatively high α-olefin content.

The catalyst according to the invention comprises a metallocene complex, a co-catalyst and optionally an inorganic support material.

The metallocene complex is chosen from the group consisting of a metallocene complex according to formula I or a metallocene complex according to formula II,

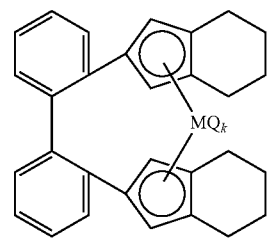

formula I

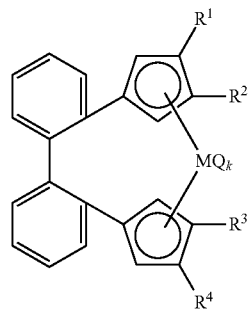

formula II wherein M is chosen from the group of Ti, Zr and Hf; Q is halogen (F, Cl, Br, I) or an alkyl group comprising 1 to 20 carbon atoms; k is the number of Q groups, is an integer and equals the valence of M minus 2; and wherein $R^1$, $R^2$, $R^3$ and $R^4$ are identical or different and can be chosen from alkyl groups with 1-20 carbon atoms, more preferably $R^1$, $R^2$, $R^3$ and $R^4$ are identical or different and are chosen from methyl or ethyl groups, most preferably $R^1$, $R^2$, $R^3$ and $R^4$ are methyl groups.

The metal M is preferably chosen from the group consisting of Ti, Zr and Hf, more preferably the metal is Zr.

Q is an anionic ligand to M. The Q ligands preferably are the same and are selected from the group consisting of halogen (F, Cl, Br, I) and alkyl groups comprising 1 to 20 carbon atoms. More preferably the Q ligands are Cl or a methyl group.

k is the number of Q groups and equals the valence of M minus 2; k is an integer. Preferably, k is 2.

The catalyst according to the invention comprises a co-catalyst. The co-catalyst employed according to the present invention can be an aluminium- or boron-containing co-catalysts. Suitable aluminium-containing co-catalysts comprise aluminoxanes and alkyl aluminium. The aluminoxanes usable according to the present invention are well known and preferably comprise oligomeric linear and/or cyclic alkyl aluminoxanes represented by the formula: $R^6$—($AlR^6$—O)$_n$—$AlR^6_2$ for oligomeric, linear aluminoxanes and (—$AlR^6$—O—)$_m$ for oligomeric, cyclic aluminoxanes; wherein n is 1-40, preferably n is 10-20; m is 3-40, preferably m is 3-20 and $R^6$ is a $C_1$ to $C_8$ alkyl group and preferably a methyl group. Further other organoaluminum compounds can be used such as trimethylaluminum, triethylaluminium, triisopropylaluminium, tri-n-propylaluminium, triisobutylaluminium, tri-n-butylaluminium, triamylaluminium; dimethylaluminium ethoxide, diethylaluminium ethoxide, diisopropylaluminium ethoxide, di-n-propylaluminium ethoxide, diisobutylaluminium ethoxide and di-n-butylaluminium ethoxide; dimethylaluminium hydride, diethylaluminium hydride, diisopropylaluminium hydride, di-n-propylaluminium hydride, diisobutylaluminium hydride, di-n-butylaluminium hydride and tetra-isobutylaluminoxane.

Suitable boron-containing co-catalysts include trialkylboranes, for example trimethylborane or triethylborane and/or perfluorophenylborane and/or a perfluorophenylborate.

In the process for the preparation of olefin polymers by polymerizing one or more olefins in the presence of a catalyst, preferably an organoaluminum co-catalyst is present.

More preferably, methylaluminoxane (MAO) is used as the co-catalyst.

In one embodiment a catalyst is formed from the metallocene complex as described above and the co-catalyst. This catalyst may be used in a solution polymerization of olefins.

In a preferred embodiment, the catalyst comprises an inorganic support material.

The catalyst that is used in the process for the preparation of olefin polymers according to the invention preferably comprises an inorganic support material. When a support material is present, the support material is preferably an inert support material, more preferably a porous inert support material. Examples of porous inert support materials are talc and inorganic oxides. Preferably, the support material is in a finely divided form.

Suitable inorganic oxide materials include group 2A, 3A, 4A and 4B metal oxides such as silica, alumina and mixtures thereof. Other inorganic oxides that may be employed either alone or in combination with the silica or alumina are magnesia, titania, zirconia and the like. Preferably, the catalyst comprises a support material and the support material is alumina or silica, more preferably a silica, most preferably a silica having a surface area between 200 and 900 m$^2$/g and a pore volume between 0.5 and 4 ml/g.

The invention is also directed to a process for the preparation of the catalyst.

In one embodiment this process comprises the steps of
a. a solution of the co-catalyst in a solvent is reacted with the metallocene complex to form a pre-catalyst solution,
b. the pre-catalyst solution is added to the inorganic support material to form a pre-catalyst mixture and
c. the pre-catalyst mixture is stirred at elevated temperature under vacuum to form the catalyst.

In a second embodiment, the process to prepare the catalyst comprises the steps of
a. providing a cocatalyst, an inorganic support material and a metallocene complex
b. adding a solution of the cocatalyst in a solvent to the inorganic support to give a treated support
c. adding the metallocene complex to the treated support to give a pre catalyst mixture
d. stirring the pre catalyst mixture at elevated temperature under vacuum to form the catalyst.

The metallocene complexes according to formula I can, for example, be prepared according to a process as described in 'Synthesis, structure, and properties of chiral titanium and zirconium complexes bearing biaryl strapped substituted cyclopentadienyl ligands', W. W. Ellis et al, Organometallics 1993, 12, 4391-4401. The solvent used in the process to prepare the catalyst complex is preferably an aprotic organic solvent.

Preferably the solvent is selected from aromatic solvents like benzene, toluene, xylene or aliphatic solvents like C6-C15 alkanes. The preferred solvent is chosen from toluene, xylene, hexane and heptane.

The preferred Al/Zr molar ratio to be employed in the process for preparing the catalyst complex is between 10 and 1000, more preferably between 50 and 500, most preferably between 75 and 300.

Elevated temperature means a temperature between 20 and 150° C., preferably between 40 and 100° C.

The metallocene complexes according to formula II can, for example, be prepared according to a process as described in 'Biphenyl-bridged metallocene complexes of titanium, zirconium, and vanadium: syntheses, crystal structures and enantioseparation', M. E. Huttenloch et al., J. of Organometallic Chemistry 541 (1997), 219-232.

In the process to produce olefin copolymers the olefins which are polymerized are ethylene and at least one α-olefin. Examples of α-olefins are propylene, 1-butene, 1-pentene, 4-methyl-1-pentene, 1-hexene, 1-octene, 1-nonene, 1-decene and styrene; conjugated and non-conjugated dienes such as butadiene, 1,4-hexadiene, 5-ethylidene-2-norbornene, dicyclopentadiene, 4-methyl-1,4-hexadiene and 7-methyl-1,6-octadiene; and cyclic olefins such as cyclobutene, but is not limited thereto. The α-olefins may optionally contain heteroatoms, like for example O, N, S and P.

Preferably, the α-olefin is chosen from 1-butene, 1-hexene or 1-octene, more preferably the α-olefin is 1-hexene.

Different types of polyethylene can be prepared with the process according to the invention. For example HDPE, MDPE, LLDPE, VLDPE which have a narrow molecular weight distribution, a relatively high molecular weight and a narrow compositional distribution.

For example an LLDPE having a melt mass flow rate (also known as melt flow index) as determined using ASTM D1238-10 (190° C./2.16 kg) which ranges from 1 to 125 g/10 min and a density in the range from 870 kg/m$^3$ to less than 940 kg/m$^3$ as determined using ASTM D1505-10 may be obtained. For example, the density of the linear low density polyethylene ranges from about 900 kg/m$^3$ to less than 940 kg/m$^3$, for example between 915 and 925 kg/m$^3$.

For example, the melt flow index of the linear low density polyethylene ranges from 0.3 to 3 g/10 min, for example from 0.5 to 1.5 g/10 min.

The ethylene α-olefin copolymer comprises at least 0.6 wt % α-olefin, preferably at least 1.5 wt %, or 2.5 wt %. In general, the amount of α-olefin in the ethylene α-olefin copolymer is less than 20 wt %, or 18 wt % or 15 wt %.

The α-olefin comonomer can be present in an amount of about 0.6 to about 20 percent by weight of the ethylene-α-olefin copolymer, more preferably in an amount of from about 1.5 to 18 wt %, or from about 2.5 to about 15 wt % of the ethylene-α-olefin copolymer.

The solvent or dispersant used in the process to produce olefin polymers may be any organic solvent usually used for the polymerization. Examples of solvents are benzene, toluene, xylene, butane, pentane, hexane, heptane, cyclohexane and methylene chloride. The polymerization can also be carried out in a process wherein the monomers are solvents or dispersants.

In the process to produce olefin polymers, the polymerization conditions, like for example temperature, time, pressure, monomer concentration can be chosen within wide limits. The polymerization temperature is in the range from −100 to 300° C., preferably 0 to 200° C., more preferably 50 to 120° C. The polymerization time is in the range of from 10 seconds to 20 hours, preferably from 1 minute to 10 hours, more preferably from 5 minutes to 5 hours. The ethylene pressure during polymerization is in the range from 1 to 3500 bar, preferably from 1 to 2500 bar, more preferably from 1 to 1000 bar, even more preferably from 1 to 500 bar, most preferably from 1 to 100 bar. The molecular weight of the polymer can be controlled by use of hydrogen in the polymerization. The polymerization may be conducted by a batch process, a semicontinuous process or a continuous process and may also be conducted in two or more steps of different polymerization conditions. The polyolefin produced is separated from the polymerization solvent and dried by methods known to a person skilled in the art.

The polymerization may be performed via a gas phase process or via a slurry process.

The production processes of polyethylene are summarised in "Handbook of Polyethylene" by Andrew Peacock (2000; Dekker; ISBN 0824795466) at pages 43-66. The catalysts can be divided in three different subclasses including Ziegler Natta catalysts, Phillips catalysts and single site catalysts. The latter class is a family of different classes of compounds, metallocene catalysts being one of them. As elucidated at pages 53-54 of said Handbook a Ziegler-Natta catalysed polymer is obtained via the interaction of an organometallic compound or hydride of a Group I-III metal with a derivative of a Group IV-VIII transition metal. An example of a (modified) Ziegler-Natta catalyst is a catalyst based on titanium tetra chloride and the organometallic compound triethylaluminium. A difference between metallocene catalysts and Ziegler Natta catalysts is the distribution of active sites. Ziegler Natta catalysts are heterogeneous and have many active sites. Consequently polymers produced with these different catalysts will be different regarding for example the molecular weight distribution and the comonomer distribution.

The various processes may be divided into solution polymerisation processes employing homogeneous (soluble) catalysts and processes employing supported (heterogeneous) catalysts. The latter processes include both slurry and gas phase processes. The invention is also directed to a olefin polymer, for example polyethylene, preferably HDPE, LLDPE, MDPE, and VLDPE obtainable or obtained by the process of the invention, for example by copolymerizing ethylene and at least one a-olefin in the presence of a catalyst according to the invention.

As defined herein, in linear polyethylene, the term "linear" means that the polymer is substantially linear, and may contain long chain branches.

"Long chain branching" (LCB) means a chain length longer than the short chain branch that results from the incorporation of the α-olefin(s) into the polymer backbone. Each long chain branch will have the same comonomer distribution as the polymer backbones and can be as long as the polymer backbone to which it is attached.

As a practical matter, current $^{13}$C nuclear magnetic resonance spectroscopy cannot distinguish the length of a long chain branch in excess of six carbon atoms. However, there are other known techniques useful for determining the presence of long chain branches in ethylene polymers. Two such methods are gel permeation chromatography coupled with a low angle laser light scattering detector (GPC-LALLS) and gel permeation chromatography coupled with a differential viscometer detector (GPCDV). The use of these techniques for long chain branch detection and the underlying theories have been well documented in the literature.

See, for example, Zimm, G. H. and Stockmayer, W. H., J. Chem. Phys., 17,1301 (1949) and Rudin, A., Modern Methods of Polymer Characterization, John Wiley & Sons, New York (1991 pp. 103-112), ), or for example: Doerpi-nghaus, P. J., Baird, G. B., J. Rheol. 47(3), 717-736 (2003).

It has been found that with the metallocene complex of the invention or with the composition of the invention wherein the metallocene complex of the invention is present on a support, it is possible to produce polyethylene from ethylene and at least one α-olefin, for example an α-olefin having up to 8 carbon atoms, with a high incorporation of the at least one α-olefin.

The amount of incorporation of the at least one a-olefin, for example an α-olefin in the polyethylene can be expressed by the amount of branches per 1000 carbon atoms. The presence of short chain branching of up to 6 carbon atoms in length can be determined in ethylene polymers by using $^{13}$C nuclear magnetic resonance (NMR) spectroscopy and is quantified using the method described by Randall (Rev. Macromol. Chem. Phys., C.29, V. 2 & 3, p. 285-297).

The low density polyethylene, for example LLDPE, preferably has an amount of branches per 1000 carbon atoms as determined using $^{13}$C NMR of at least 0.4, for example of at least 0.6, for example at least 1 and/or for example at most 25, for example at most 20, for example at most 15.

The number average molecular weight (Mn) of the ethylene copolymer of the invention may vary between wide ranges and may for example be in the range from 25000 to 800000 Da.

For example, the Mn of the polyolefin of the invention may be at least 30000, for example at least 40000, for example at least 60000, for example at least 90000 and/or for example at most 500000, for example at most 400000, for example at most 300000, for example at most 200000.

The weight average molecular weight (Mw) of the polyolefin, for example polyethylene, for example LLDPE of the invention may also vary between wide ranges and may for example be in the range from 80000 to 900000 Da. For example, the Mw of the polyolefin of the invention may be at least 100000, for example at least 120000, for example at least 140000, for example at least 160000 and/or for example at most 800000, for example at most 700000, for example at most 600000, for example at most 500000.

The molecular weight distribution (that is Mw/Mn) of the polyolefin of the invention may for example vary from 2 to 5, from 2.1 to 4, or from 2.5 to 3.5.

For purpose of the invention, the Mw and Mn are determined using SEC (Size Exclusion Chromatography) using 1,2,4-trichlorobenzene as an eluent, and calibrated using linear polyethylene standards.

The crystallinity temperature (Tc) of the polyolefin of the invention may for example be in the range from 70 to 125° C., or 90 to 120° C. The melt temperature (Tm) of the polyolefin of the invention may for example be in the range from 80 to 145° C., or from 100 to 140° C.

For purpose of the invention, the $T_m$ and $T_c$ are determined using Differential Scanning calorimetry according to ASTM D 3418-08 using a scan rate of 10° C./min on a sample of 10 mg and using the second heating cycle.

The ethylene copolymers prepared in the process of the present invention show a remarkable narrow CCD (chemical composition distribution). It is known that many conventional metallocene catalysts make well defined polymers. Many of these polymers have however drawbacks, like for example low molecular weight, low activity, sometimes broad molecular weight distributions. Catalysts having a 2,2'-biphenyl bridge show a number of advantages, like high activity, narrow molecular weight distribution, high molecular weight and excellent a-olefin incorporation. Unfortunately the inventors discovered that this class of metallocene catalysts makes products having a broad CCD: either a broad CCD peak is present within a temperature range between 35 and 120° C., or at least 2 separate peaks can be seen. In the prior art, no clues are present how to solve this problem. The inventors discovered after preparation of many metallocene complexes that the catalysts as described in claim 1 solve the problem, and present a single peak in CEF.

This peak is narrow, which can be expressed as a Broadness Index (BI) below 5, preferably <4, more preferably <3.5 In general the BI will be at least 1, or >1.1 or preferably >1.2.

The broadness Index BI of the peak in CEF is defined as the ratio ($PW_{20\%}/PW_{80\%}$), wherein $PW_{20\%}$ is defined as the peak width at 20% of the peak height $P_H$ at the peak maximum $P_{MAX}$, and wherein $PW_{80\%}$ is defined as the peak width at 80% of the peak height $P_H$ at the peak maximum $P_{MAX}$. The peak height $P_H$ is defined as the maximum peak height of a peak in CEF, which can be found at the peak maximum $P_{MAX}$. The measurement of the different parameters is shown in FIG. 1.

The polyolefin obtained or obtainable by the process of the invention may be mixed with suitable additives.

Examples of suitable additives for polyethylene include but are not limited to the additives usually used for polyethylene, for example antioxidants, nucleating agents, acid scavengers, processing aids, lubricants, surfactants, blowing agents, ultraviolet light absorbers, quenchers, antistatic agents, slip agents, anti-blocking agents, antifogging agents, pigments, dyes and fillers, and cure agents such as peroxides. The additives may be present in the typically effective amounts well known in the art, such as 0.001 weight % to 10 weight % based on the total composition.

The polyolefins of the invention and compositions comprising said polyolefins may suitably be used for the manufacture of articles. For example, the polyolefins and compositions of the invention may be manufactured into film, for example by compounding, extrusion, film blowing or casting or other methods of film formation to achieve, for example uniaxial or biaxial orientation. Examples of films include blown or cast films formed by coextrusion (to form multilayer films) or by lamination and may be useful as films for packaging, for example as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Other applications may be blow moulding bottles, pipes, caps, closures and the like.

Therefore, in another aspect, the invention also relates to articles comprising the polyolefins obtainable by the process of the invention.

In yet another aspect, the invention also relates to use of the olefin polymers obtainable by the process according to the invention for the preparation of articles, for example for the preparation of films.

In yet another aspect, the invention relates to a process for the preparation of articles using the polyolefin according to the invention.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

FIGURES

FIG. 3-8 show CEF curves of ethylene copolymers prepared with different catalysts, both catalysts according to the process of the present invention (I and II), and catalysts not according to the process of the present invention.

EXAMPLES

Figure 1:
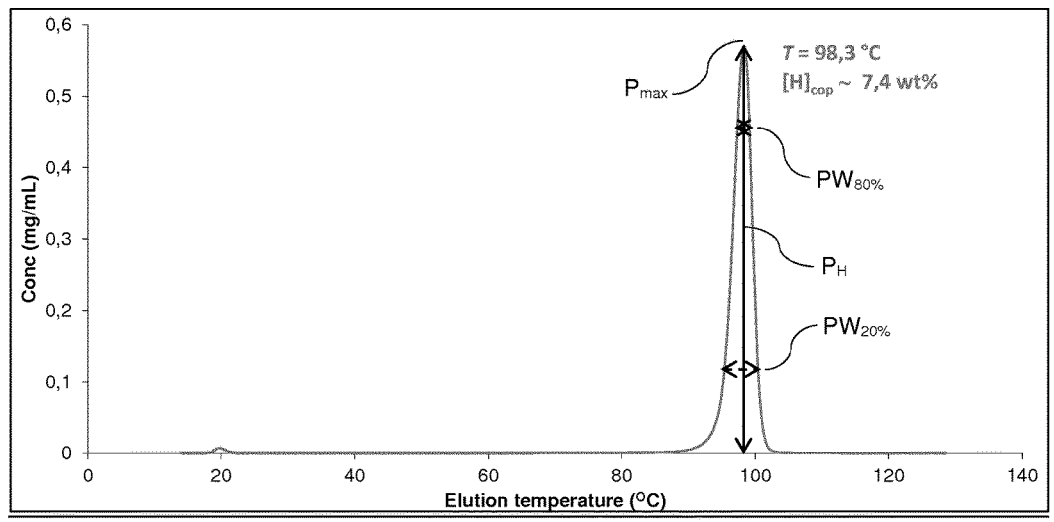
FIG. 1 shows elements of the broadness index BI parameter in a CEF diagram

Test Methods
Melt Index
The melt index is measured according to ASTM D-1238-10 Condition F (190° C., 21.6 kg).

Density

The density is determined according to ISO1872-2. The samples were prepared and pressed according to ISO1872-2 and annealed by boiling in water for half an hour, then left to cool for 16 hours in the same water after which the samples were measured.

Molecular Weight Distribution.

Sample preparation: The polymer samples were dissolved (0.1 w %) in 1,2,4-trichlorobenzene (TCB), which was distilled prior to use, over a period of 4 h at 150° C. under nitrogen and stabilized with di-tertbutylparacresol (DBPC) at a concentration of 1 g/L. The solutions were filtered at high temperature (150° C.) using a millipore filtration setup (1.2 µm) positioned in a Hereous LUT oven operating at 150° C.

SEC-DV measurement: The separation of the polymer according to molar mass is performed with a PL-GPC220 equipped with PL BV-400 viscosimeter and refractive index detector. This SEC system is operated at high temperature (column compartment at 150° C., injector compartment at 150° C., and solvent reservoir at 60° C.) and a flow of 1.0 mL/min. Four Polymer Laboratories GPC columns (PL 13 µm mixed Olexis columns) were used. Calculations were performed with Viscotek TriSEC 2.7 software. The eluent used was 1,2,4-trichlorobenzene. The columns were calibrated using linear polyethylene standards.

Branches/1000 C

The amount of branches is determined with the aid of FTIR.

FTIR of the resulting polymers were measured by converting the PE powder in to a hot-pressed thin film. The film is measured in transmission IR mode. The height of a band corresponding to CH3 bending vibrations (~1380-1375 cm-1) is measured and corrected for the film-thickness using 4400-4000 cm-1 spectral region. The obtained value is then compared with a calibration line. The calibration line is established upfront using reference ethylene/1-olefin polymers characterized by 13C NMR.

Example 1

Preparation of Silica Supported Metallocene Catalysts

The immobilization of the single site catalyst, 2,2'-biphenyl-(2-tetrahydroindenyl)$_2$ZrCl$_2$ (catalyst I) on silica was performed using Incipient Wetness technique and it involves the following steps:

A solution of methylaluminoxane (MAO) in toluene (7.6 mL, 30 wt %) was added to 0.244 mmol of single site catalyst and the solution was stirred at room temperature for 30 min.

The MAO/single site catalyst solution was added drop wise to 5.0 g of silica (ES70X (Grace), activated at 600° C. for 4 h) while the mixture was stirred mechanically (Incipient Wetness)

The mixture was stirred at 50° C. for 1 h. Volatiles were evaporated in vacuo at 75° C. for 1 h The elemental composition of the supported catalyst I was measured with x-ray diffraction (XRF); see Table 1.

The immobilization of the metallocene complex, {2,2'-biphenyl-(3,4-dimethylcyclopentadienyl)$_2$ZrCl$_2$} (metallocene II) on silica was performed using the following steps:

A solution of methylaluminoxane (MAO) in toluene (7.6 mL, 30 wt %) was added to 0.244 mmol of (metallocene 1) and the solution was stirred at room temperature for 30 min.

The MAO/metallocene 1 solution was added drop wise to 5.0 g of silica (ES70X (Grace), activated at 600° C. for 4 h) while the mixture was stirred mechanically The mixture was stirred at 50° C. for 1 h. Volatiles were evaporated in vacuo at 75° C. for 1 h In order to compare the catalyst performance, two catalysts described in prior art patents were also immobilized on silica using the same process as described above. The catalysts investigated are 2,2'-biphenyl-(2-Indenyl)$_2$ZrCl$_2$ (catalyst III, Reference patent: U.S. Pat. No. 6,342,622 B1) and 1,2-cyclohexyl-(2-tetrahydroindenyl)$_2$ZrCl$_2$ (catalyst V).

The elemental compositions of the catalysts determined with XRF are given below:

TABLE 1

| Cat ID | Cat | Al wt % (exp) | Si wt % (exp) | Zr wt % (exp) |
|---|---|---|---|---|
| I | 2,2'-Biph-(2-tetrahydroindenyl)$_2$ZrCl$_2$ | 12.5 (13.7) | 29.6 (32.3) | 0.28 (0.309) |
| II | 2,2'-Biph-(3,4-Me$_2$Cp)$_2$ZrCl$_2$ | 13.0 (13.7) | 30.0 (32.3) | 0.30 (0.309) |
| III | 2,2'-Biph-(2-Ind)$_2$ZrCl$_2$ | 12.3 (13.7) | 30.1 (32.3) | 0.29 (0.309) |
| IV | 1,2-Ph-(2-Ind)$_2$ZrCl$_2$ | 12.5 (13.7) | 30.2 (32.3) | 0.24 (0.309) |
| V | 1,2-cyclohexyl-(2-tetrahydroindenyl)$_2$ZrCl$_2$ | 14.4 (13.7) | 32.2 (32.3) | 0.36 (0.309) |

Example 2

Polymerizations

Ethylene Homopolymerization Procedure

The polymerizations were carried out in a 5 L bench scale batch reactor. The reactor operates under slurry conditions using isobutane as diluent. The 5 liter reactor is filled to 65% of its volume with diluent prior to each experiment. Alkylamine ethoxylate (Atmer® 163) premixed with 2 equivalents of triisobutylaluminium (TiBA) was used as antifouling agent and TiBA was used as scavenger (0.017 mmol/L). The temperature of the reactor was kept as constant as possible by a thermostat bath. About 100 mg of the immobilised catalysts was then injected into the reactor, and constant ethylene pressure was maintained. After 1 hour of reaction time, the polymers were collected and dried in a vacuum oven (60° C., overnight) before the further analysis.

Ethylene/1-Hexene Copolymerization

Copolymerizations were carried out in the same experimental set up used for homopolymerization. The same polymerization protocols were used except that a specific amount of 1-hexene was fed into the reactor prior to the ethylene feed. After 1 hour of reaction time, the polymers were collected and dried in a vacuum oven (60° C., overnight) before further analysis.

TABLE 2

Homo and copolymerization results

| Ex | Cat ID | 1-hexene (mL) | Activity (gPE/gcat) | MFI 21.6 | Density | Branches/ 1000 C | Mw (kg/mol) | Mn (kg/mol) | Mw/Mn |
|---|---|---|---|---|---|---|---|---|---|
| 1 | I | 0 | 2173 | <1 | 942 | — | 380 | 123 | 3.1 |
| 2 | I | 25 | 2000 | <1 | 935 | 0.6 | 350 | 110 | 3.2 |
| 3 | I | 75 | 2059 | <1 | 930 | 2.1 | 350 | 109 | 3.2 |
| 4 | II | 0 | 632 | <1 | 941 | — | 450 | 145 | 3.1 |
| 5 | II | 25 | 938 | <1 | 930.4 | 0.7 | 440 | 125 | 3.5 |
| 6 | II | 75 | 726 | <1 | 921.4 | 2.4 | 390 | 100 | 3.8 |
| A1 | III | 0 | 2766 | 2.3 | 948 | — | 310 | 61 | 5.0 |
| A2 | III | 25 | 3850 | 4.9 | 941.2 | Nd | 270 | 57 | 4.6 |
| A3 | III | 75 | 1049 | 3.9 | 936 | 1.6 | 170 | 54 | 3.2 |
| B1 | IV | 0 | 4500 | — | 966 | — | 22 | 7.4 | 3.2 |
| B2 | IV | 75 | 6310 | — | 951 | 6.0 | 20 | 7.3 | 3.1 |
| C1 | V | 0 | 301 | 3.8 | 963 | — | 120 | 22 | 5.4 |
| C2 | V | 75 | 243 | 5.6 | 956 | 2.3 | 60 | 16 | 3.8 |

Polymerization Temperature = 80° C., Polymerization time = 1 hour, isobutene is used as diluent.

A comparison between examples 1-6 and comparative experiments A1-3, B1-2 and C1-C2 shows that in all cases catalysts I and II make polymers having a higher molecular weight and/or narrow Mw/Mn than the comparison catalysts III-V.

Moreover the catalyst I and II are able to incorporate a higher amount of comonomer, making a polymer having a lower density compared to the catalysts III.

Example 3

Temperature Sensitivity of Catalyst II

Copolymerizations were carried out in the same experimental set up used for homopolymerization. The same polymerization protocols were used except that polymerization temperatures have been varied. After 1 hour of reaction time, the polymers were collected and dried in a vacuum oven (60° C., overnight) before further analysis.

TABLE 3

Effect of the temperature on the performance of catalyst II

| Ex | cat ID | 1-hexene (mL) | Temp (° C.) | Activity (gPE/gcat) | MFI 21.6 | density |
|---|---|---|---|---|---|---|
| 4 | II | 0 | 80 | 632 | <1 | 941 |
| 7 | II | 0 | 87 | 1429 | 0.12 | 942.4 |
| 8 | II | 0 | 95 | 1543 | 0.20 | 941 |
| 5 | II | 75 | 80 | 726 | <1 | 921.4 |
| 9 | II | 75 | 87 | 1398 | 0.13 | 922.3 |
| 10 | II | 75 | 95 | 1396 | 0.43 | 923.5 |

Figure 2:
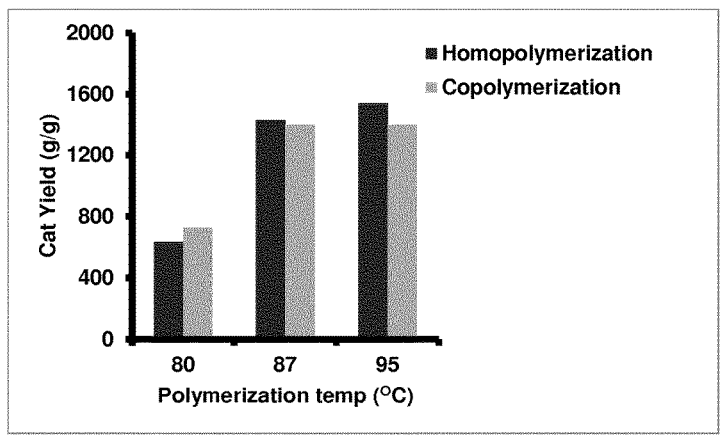
FIG. 2 shows activities of catalyst II as a function of the polymerization temperature

FIG. 2 shows the thermal stability of catalyst II during homopolymerization of ethylene and the copolymerization of ethylene and 1-hexene. The productivity increases with an increasing polymerization temperature. When the catalyst is used for copolymerization of ethylene and 1-hexene a slow decrease in molecular weight is observed as temperature goes up, when compared with the molecular weight obtained for ethylene homopolymers. This is consistent with the somewhat higher MFI values for the copolymers according to Table 3.

Example 4

Determination of CCD with Products Obtained with Selective Catalysts

Example 4 describes the polymerization of unsupported single-site catalyst in PPR, and specific methods used for polymer characterization (GPC, NMR, polymerization protocol) and CEF experimental details.

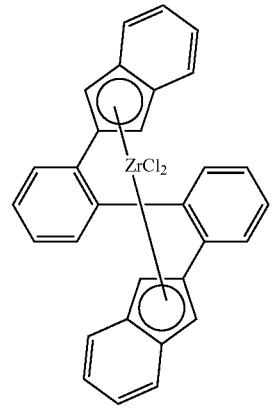

III

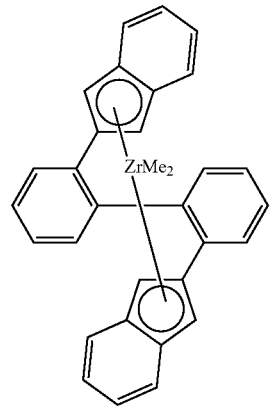

VI

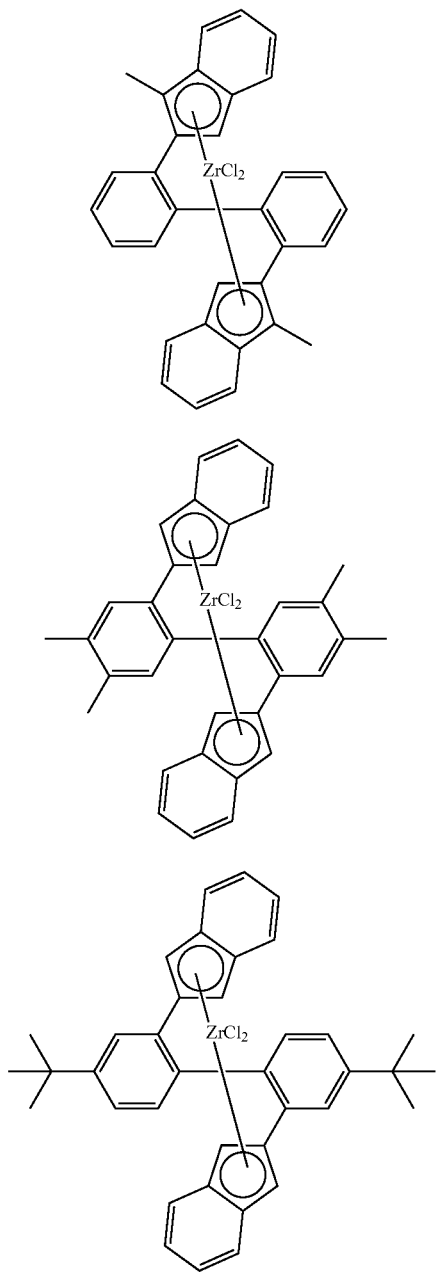

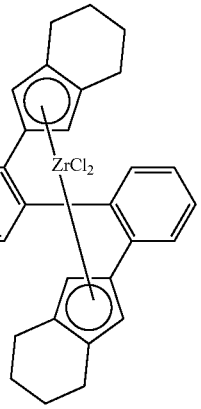

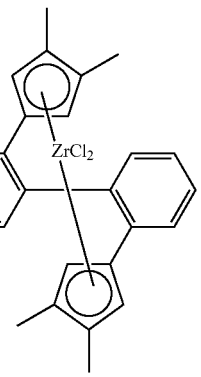

Cat III, VI, VII, VIII, IX are 1,2-biphenyl bridged catalysts that display broad CCD, having either 2 peaks between 35 and 120° C. or a broad multimodal peak in CEF. Catalysts I and II give an exceptionally narrow CCD with a single peak in CEF between 35 and 120° C.

TABLE

| | | Ethylene polymerization in PPR- unsupported catalysts | | | | | | |
|---|---|---|---|---|---|---|---|---|
| Ex | Cat code | Catalyst | *Rp | Mw (kg/mol) | PDI | C6 (mol %) | No of peaks in CEF | Elution temp in CEF (° C.) | BI |
| 11 | I | Biph(2-THI)$_2$ZrCl$_2$ | 326 | 260 | 2.5 | 1 | 1 | 98.3 | 2 |
| 12 | II | Biph(2-3,4-Me$_2$Cp)$_2$ZrCl$_2$ | 105 | 202 | 2.3 | 4.2 | 1 | 83.5 | 2.6 |
| D1 | III | Biph(2-Ind)$_2$ZrCl$_2$ | 160 | 222 | 3.0 | 4 | 2 | 95, 72.7 | — |
| D2 | VI | Biph(2-Ind)$_2$ZrMe$_2$ | 126 | 180 | 3.0 | 3.4 | 2 | 95.4, 73.4 | — |
| D3 | IX | $^{tBu}$Biph(2-Ind)$_2$ZrCl$_2$ | 161 | 161 | 2.4 | 4.1 | 2 | 94.9, 71 | — |

TABLE-continued

Ethylene polymerization in PPR- unsupported catalysts

| Cat Ex code | Catalyst | *Rp | Mw (kg/mol) | PDI | C6 (mol %) | No of peaks in CEF | Elution temp in CEF (° C.) | BI |
|---|---|---|---|---|---|---|---|---|
| D4 VIII | Me$_2$Biph(2-Ind)$_2$ZrCl$_2$ | 339 | 339 | 3.1 | 4.4 | 2 | 75.1, 98 | — |
| D5 VII | Biph(2-MeInd)$_2$ZrCl$_2$ | 134 | 134 | 3.1 | 2.2 | Broad-multimodal | 80-108 | 6.3 |

*Rp = Productivity in kg mmol$_{cat}^{-1}$ [C$_2$H$_4$]$^{-1}$ h$^-$, Polymerization time = 30 min, temperature = 80° C., MAO = 2 mM.

The polymerization for example 5 was performed according to the following procedure:

PPR Polymerization Protocols

Prior to the execution of a library, the 48 PPR cells (reactors) undergo 'bake-and-purge' cycles overnight (8 h at 90-140° C. with intermittent dry N$_2$ flow), to remove any contaminants and left-overs from previous experiments. After cooling to glove-box temperature, the stir tops are taken off, and the cells are fitted with disposable 10 mL glass inserts and PEEK stirring paddles (previously hot-dried under vacuum); the stir tops are then set back in place, the cells are loaded with the proper amounts of toluene (in the range 2.0-3.5 mL), 1-hexene (in the range 0.5-2.0 mL) and MAO solution (100 μL of 0.1 mol L$^{-1}$ in toluene), thermostated at 80° C., and brought to the operating pressure of 65 psig with ethylene. At this point, the catalyst injection sequence is started; proper volumes of a toluene 'chaser', a solution of the precatalyst in toluene (typically in the range 0.01-0.05 mmol L$^{-1}$), and a toluene 'buffer' are uptaken into the slurry needle, and then injected into the cell of destination. The reaction is left to proceed under stirring (800 rpm) at constant temperature and pressure with continuous feed of ethylene for 30 min, and quenched by over-pressurizing the cell with dry air (preferred to other possible catalyst poisons because in case of cell or quench line leaks oxygen is promptly detected by the dedicated glove-box sensor).

After quenching, the cells are cooled down and vented, the stir-tops are removed, and the glass inserts containing the reaction phase are taken out and transferred to a Genevac EZ2-Plus centrifugal evaporator, where all volatiles are distilled out and the polymers are thoroughly dried overnight. Reaction yields are double-checked against on-line monomer conversion measurements by robotically weighing the dry polymers in a Bohdan Balance Automator while still in the reaction vials (subtracting the pre-recorded tare). Polymer aliquots are then sampled out for the characterizations.

The samples prepared according to this procedure in example 5 have been analysed according to the following methods:

GPC Analysis

GPC curves are recorded with a Freeslate Rapid GPC setup, equipped with a set of 2 mixed-bed Agilent PLgel 10 μm columns and a Polymer Char IR4 detector. The upper deck of the setup features a sample dissolution station for up to 48 samples in 10 mL magnetically stirred glass vials, 4 thermostated bays each accommodating 48 polymer solutions in 10 mL glass vials, and a dual arm robot with two heated injection needles. With robotic operation, pre-weighed polymer amounts (typically 1-4 mg) are dissolved in proper volumes of orthodichlorobenzene (ODCB) containing 0.40 mg mL$^{-1}$ of 4-methyl-2,6-di-tert-butylphenol (BHT) as a stabilizer, so as to obtain solutions at a concentration of 0.5 to 1.0 mg mL$^{-1}$. After 2 h at 150° C. under gentle stirring to ensure complete dissolution, the samples are transferred to a thermostated bay at 145° C., and sequentially injected into the system at 145° C. and a flow rate of 1.0 mL min$^{-1}$. In post-trigger delay operation mode, the analysis time is 12.5 min per sample. Calibration is carried out with the universal method, using 10 monodisperse polystyrene samples (M$_n$ between 1.3 and 3700 KDa). Before and after each campaign, samples from a known i-PP batch produced with an an sa-zirconocene catalyst are analyzed for a consistency check.

NMR Characterizations $^{13}$C NMR spectra are recorded with a Bruker Avance 400 III spectrometer equipped with a 5 mm High Temperature Cryoprobe, and a robotic sample changer with pre-heated carousel (24 positions). The samples (20-30 mg) are dissolved at 120° C. in tetrachloroethane-1,2-d$_2$ (0.6 mL), added with 0.40 mg mL$^{-1}$ of BHT as a stabilizer, and loaded in the carousel maintained at the same temperature. The spectra are taken sequentially with automated tuning, matching and shimming. Typical operating conditions for routine measurements are: 45° pulse; acquisition time, 2.7 s; relaxation delay, 5.0 s; 400-800 transients (corresponding to an analysis time of 30-60 min). Broad-band proton decoupling is achieved with a modified WALTZ16 sequence (BI_WALTZ16_32 by Bruker).

CEF Method—Experimental

Chemical composition distributions of the produced polymers were analyzed by Crystallization Elution Fractionation (CEF, PolymerChar, Valencia, Spain) hyphenated with IR5 detector. Polymer solutions were prepared at 1 mg/mL concentration level in o-dichlorobenzene (ODCB), stabilized with 0.5 mg/mL of 2,6-Di-tert-butyl-4-methylphenol (BHT) and agitated for at least 2 hours at 150° C. in the auto sampler oven. The polymer solutions were, then, injected into the system at 95° C. and pumped through CEF column while being cooled down to 35° C. at a cooling rate of 2° C./min and a flow rate of 0.05 mL/min. Finally, the samples were eluted out by pumping oDCB at a flow rate of 1 mL/min, while the column was heated to 155° C. with 4° C./min.

The CEF diagrams of the different samples have been enclosed in FIGS. 3-8.

The invention claimed is:

1. A process for the preparation of ethylene α-olefin copolymers, the process comprising copolymerizing ethylene with α-olefins in the presence of a catalyst formed by contacting a metallocene complex with a cocatalyst,
wherein the metallocene complex is chosen from the group consisting of a metallocene complex according to formula I or a metallocene complex according to formula II,

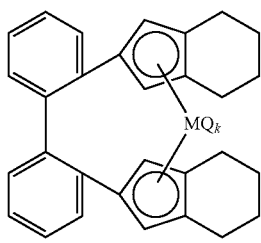

formula I

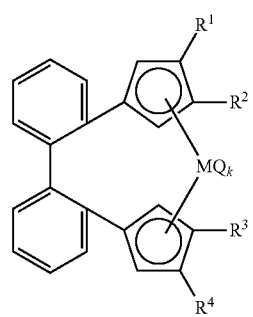

formula II wherein
M is chosen from the group of Ti, Zr and Hf; Q is halogen or an alkyl group comprising 1 to 20 carbon atoms;
k is the number of Q groups, is an integer and equals the valence of M minus 2; and
$R^1$ $R^2$, $R^3$ and $R^4$ are identical or different and are chosen from alkyl groups comprising 1-20 carbon atoms.

2. The process according to claim 1, wherein the metallocene complex is chosen from the group consisting of a metallocene complex according to formula I or a metallocene complex according to formula II,

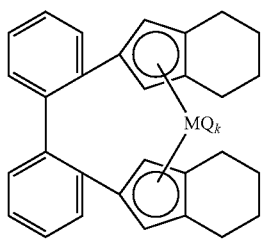

formula I

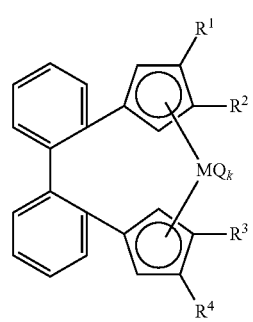

formula II wherein
M is chosen from the group of Zr and Hf;
Q is Cl or a methyl group;
k is 2; and
$R^1$ $R^2$, $R^3$ and $R^4$ are methyl groups.

3. The process according claim 1, wherein the co-catalyst is selected from an aluminum- or boron-containing co-catalyst.

4. The process according to claim 1, wherein the catalyst comprises an inorganic support material.

5. The process according to claim 1, wherein the cocatalyst contains Al, M is Zr and wherein the Al/Zr molar ratio is between 10 and 1000.

6. The process according to claim 1, wherein the α-olefin is chosen from 1-butene, 1-hexene or 1-octene.

7. The process according to claim 1, wherein the ethylene α-olefin copolymer comprises at least 0.6 wt % α-olefin.

8. The process according to claim 1, wherein the ethylene α-olefin has a weight average molecular weight (Mw) in the range from 80000 to 900000 Da.

9. The process according to claim 1, wherein the molecular weight distribution (Mw/Mn) of the ethylene α-olefin copolymer ranges from 2 to 5.

10. The process according to claim 1, wherein the ethylene α-olefin copolymer has a narrow chemical composition distribution wherein only one peak is present in a CEF diagram within a temperature range between 35 and 120 ° C., and this single peak has a broadness index (BI) between 1 and 5, wherein BI is defined as the as the ratio ($PW_{20\%}/PW_{80\%}$), wherein $PW_{20\%}$ is defined as the peak width at 20% of the peak height $P_H$ at the peak maximum $P_{MAX}$, and wherein $PW_{80\%}$ is defined as the peak width at 80% of the peak height $P_H$ at the peak maximum $P_{MAX}$.

11. An article comprising an ethylene α-olefin copolymer obtained by the process according to claim 1.

12. The process according to claim 1, wherein Q is F, Cl, Br, or I or an alkyl group comprising 1 to 20 carbon atoms, and $R^1$, $R^2$, $R^3$ and $R^4$ are identical or different and are chosen from methyl or ethyl groups.

13. The process according to claim 5, wherein the Al/Zr molar ratio is between 50 and 500.

14. The process according to claim 5, wherein the Al/Zr molar ratio is between 75 and 300.

15. The process according to claim 7, wherein the ethylene α-olefin copolymer comprises at least 1.5 wt % α-olefin.

16. The process according to claim 7, wherein the ethylene α-olefin copolymer comprises at least 2.5 wt % α-olefin.

17. The process according to claim 9, wherein the molecular weight distribution (Mw/Mn) of the ethylene α-olefin copolymer ranges from 2.1 to 4.

18. The process according to claim 9, wherein the molecular weight distribution (Mw/Mn) of the ethylene α-olefin copolymer ranges from 2.5 to 3.5.

19. The process according to claim 2, wherein
the cocatalyst contains Al, M is Zr, and wherein the Al/Zr molar ratio is between 50 and 500;
the ethylene α-olefin copolymer comprises at least 1.5 wt % α-olefin;
the ethylene α-olefin has a weight average molecular weight (Mw) in the range from 80000 to 900000 Da;
the molecular weight distribution (Mw/Mn) of the ethylene α-olefin copolymer ranges from 2.1 to 4;
the ethylene α-olefin has a weight average molecular weight (Mw) in the range from 80000 to 900000 Da; and
the ethylene α-olefin copolymer has a narrow chemical composition distribution wherein only one peak is present in a CEF diagram within a temperature range between 35and 120 ° C., and this single peak has a broadness index (BI) between 1 and 5, wherein BI is defined as the as the ratio ($PW_{20\%}/PW_{80\%}$), wherein $PW_{20\%}$ is defined as the peak width at 20% of the peak height $P_H$ at the peak maximum $P_{MAX}$, and wherein $PW_{80\%}$ is defined as the peak width at 80% of the peak height $P_H$ at the peak maximum $P_{MAX}$.

20. The process according to claim 19, wherein the Al/Zr molar ratio is between 50 and 500;

the ethylene α-olefin copolymer comprises at least 2.5 wt % α-olefin; and the molecular weight distribution (Mw/Mn) of the ethylene α-olefin copolymer ranges from 2.5 to 3.5.

* * * * *